United States Patent [19]

Ono et al.

[11] Patent Number: 5,095,090

[45] Date of Patent: Mar. 10, 1992

[54] POLYPEPTIDE THIN FILM FROM AMPHIPHILIC COMPOUNDS

[75] Inventors: Mitsunori Ono; Tsutomu Miyasaka; Naoyuki Nishikawa, all of Kanagawa, Japan

[73] Assignee: Fuji Photo Film Co., Ltd., Kanagawa, Japan

[21] Appl. No.: 507,540

[22] Filed: Apr. 11, 1992

[30] Foreign Application Priority Data

Apr. 13, 1989 [JP] Japan .................................. 1-93959
Apr. 13, 1989 [JP] Japan .................................. 1-93960

[51] Int. Cl.$^5$ ............................................ C08G 69/10
[52] U.S. Cl. ................................. 528/328; 528/184; 528/310; 528/367; 528/369
[58] Field of Search ............... 528/328, 310, 184, 367, 528/369

[56] References Cited

U.S. PATENT DOCUMENTS 3,052,655  9/1962  Fox et al. ............................ 528/328
4,289,872  9/1981  Denkewalter et al. ............. 528/328

Primary Examiner—Harold D. Anderson
Attorney, Agent, or Firm—Sughrue, Mion, Zinn Macpeak & Seas

[57] ABSTRACT

A polypeptide thin film obtained by polymerizing a monomolecular film comprising a monomer mixture of (a) an amphiphilic compound having a hydrophobic moiety and a hydrophilic moiety having an amino acid ester structure per molecule, the conjugated acid of the elimination group of the ester having a pKa of not higher than 14, and (b) an amphiphilic compound having two amino groups per molecule or an amphiphilic compound having two ester structures per molecule, the conjugated acid of the elimination group of the ester having a pKa of not higher than 16, or a built-up film of the monomolecular film; and a process for preparing a material carrying the polypeptide thin film.

3 Claims, 9 Drawing Sheets

POLYPEPTIDE THIN FILM FROM AMPHIPHILIC COMPOUNDS

FIELD OF THE INVENTION

This invention relates to a thin film comprising a molecular assembly and a process for preparing a material on which the same is carried. More particularly, this invention relates to a thin film which is composed of a polymer of an amino acid having peptide bonds and which has an excellent compatibility with organisms, and a process for preparing a material on which the same is carried.

BACKGROUND OF THE INVENTION

Molecular assemblies, such as a monomolecular film (monolayer) having a molecular arrangement or built-up film (monolayers=multilayer) formed by building up a plurality of the monomolecular films, are widely employed as materials for electronics devices, materials for surface protection, hyper-filtration membranes which utilize gaseous molecule or ion-permselectivity, functional thin films for sensors and permeability-controlling films for material delivery by utilizing the ultra-thinness and denseness thereof.

The Lamgmuir-Blodgett process (LB process) is generally known as a method for building up a monomolecular film of an amphiphilic molecule formed at the gas-liquid interface on a substrate. The range of use of the various LB films prepared by this method has been increased in recent years (see, *Solid Physics* 17 (12) 45 (1982)).

The molecular assemblies comprising an LB film exhibit various functions due to the molecular orientation and ultra-thinness. However, they have disadvantages in that they are physically delicate and the film structure is liable to be broken, or they have many structural defects depending upon the compounds employed and a high density can not be obtained.

Therefore, it has been desired to provide a film which has a uniform structure with an excellent packing of molecules and an improved physical strength.

One of the effective means for physically strengthening the film structure of the molecular assembly is by crosslinking or polymerization.

With regard to the polymerization of molecular assemblies, such as an LB film, conventional polymerizable compounds employed and their polymerization are summarized in H. Bader et al., *Advances in Polymer Science*, Vol. 64, page 1 (1985) and R. Buschl, et al., *Macromol. Chem. Suppl.*, Vol. 6, page 245 (1984).

The study of polymerizable amphiphilic compounds has been active in the 1980's. Widely used methods employ unsaturated compounds such as vinyl, diene and diacetylene compounds. The unsaturated bonds are cleaved by ultraviolet light (UV) or by radiation, such as gamma rays, so as to carry out polymerization. However, these methods have difficulty in keeping the order of molecular arrangement by distortion due to polymerization after the cleavage of the unsaturated bonds, though fast polymers can be obtained.

The orientation of the film is greatly influenced by the lengths of the alkyl chains and the type of terminal hydrophilic group, as discussed in A. Laschewsky and H. Ringsdord, *Macromolecule*, Vol. 21, page 1936 (1988). Hence, compounds providing a polymerized film having good orderliness is limited to a small number of compounds.

It is disclosed in A. Laschewsky, *J. Am. Chem. Soc.*, Vol. 109, page 788 (1987) that in the amphiphilic compounds having various unsaturated bonds useful for radiation polymerization, the polymeric groups are carried through spacer groups so as to maintain order.

JP-A-57-159506 (the term "JP-A" as used herein means an "unexamined published Japanese patent application") discloses that the polymer films of the monomolecular films of unsaturated compounds (surfactants) and built-up films thereof, prepared by radiation polymerization are used as hyper-filtration films.

Conventional methods for polymerizing these compounds having unsaturated bonds by radiation have the following problems. First, turbulence in the arrangement structure or the disordered agglomeration or precipitation of molecules is liable to be caused by polymerization. Hence, the specific molecular design, for example, the introduction of spacer groups into molecules must be made to prevent such a problem arising. Second, irradiation with ultraviolet light or gamma rays poses a problem in that additives often coexisting with polymerizable amphiphilic molecules are decomposed or denatured. Third, films prepared by such a polymerization have very poor compatibility with organisms and their applications to the tissues of organisms as permeability-controlling films for medicines are limited.

Methods for forming a disulfide bond by the oxidative polymerization of dithiols are proposed in *J. Am. Chem. Soc.*, Vol. 109, page 4419 (1987) as polymerization methods which do not require radiation. Further, methods for radical polymerizing the above-described compounds having unsaturated bonds in the presence of initiators are also useful.

In these methods, however, the initiators must be used during polymerization. Hence, there must be a required stage for removing the initiators from the film-forming system after the completion of polymerization. In addition, these methods have a problem in that coexisting materials are affected by the initiators, including oxidation-reduction agents.

To improve compatibility with organisms by improving polymerization forms, methods for condensation-polymerizing the molecular films of amino acid derivatives in the presence of carbodiimide as a condensing agent are disclosed in *J. Am. Chem. Soc.*, Vol. 108, page 487 (1986). However, the method using a condensing agent has a problem in that the condensing agent and by-products are left behind and the condensation reaction is difficult to handle. This is because the efficiency of the condensation reaction must be controlled.

SUMMARY OF THE INVENTION

Accordingly, an object of the present invention is to provide a polymerizable thin film having a good molecular arrangement, which is polymerized without using radiation or a polymerization initiator, and also to provide a process for preparing a material on which the same is carried.

Another object of the present invention is to provide a polymerizable thin film which allows polymerization to proceed spontaneously at a high yield by self-polymerization, and a process for preparing a material on which the same is carried.

Still another object of the present invention is to provide a polymeric thin film having excellent compatibility with organisms.

The above objects of the present invention have been achieved by providing:

a polypeptide thin film obtained by polymerizing a monomolecular film (monolayer) comprising a monomer mixture of
  (a) an amphiphilic compound having a hydrophobic moiety and a hydrophilic moiety having an amino acid ester structure per molecule, the conjugated acid of the elimination group of the ester having a pKa of not higher than 14, and
  (b) an amphiphilic compound having two amino groups per molecule or an amphiphilic compound having two ester structures per molecule, the conjugated acid of the elimination group of the ester having a pKa of not higher than 16,
or a built-up film (multilayer) of the monomolecular film; and a process for preparing a material carrying the polypeptide film, which comprises
  (A) forming a monomolecular film comprising a monomer mixture of
    (a) an amphiphilic compound having a hydrophobic moiety and a hydrophilic moiety having an amino acid ester structure per molecule, the conjugated acid of the elimination group of the ester having a pKa of not higher than 14, and
    (b) an amphiphilic compound having two amino groups per molecule, or an amphiphilic compound having two ester structures per molecule, the conjugated acid of the elimination group of the ester having a pKa of not higher than 16,
at a gas-liquid interface, and either
  (B) polymerizing the monomolecular film at the interface and then transferring the resulting film onto a substrate, or
  (B') transferring the monomolecular film or a built-up film prepared from the monomolecular film onto a substrate, and then carrying out polymerization.

DETAILED DESCRIPTION OF THE INVENTION

Figure 1:
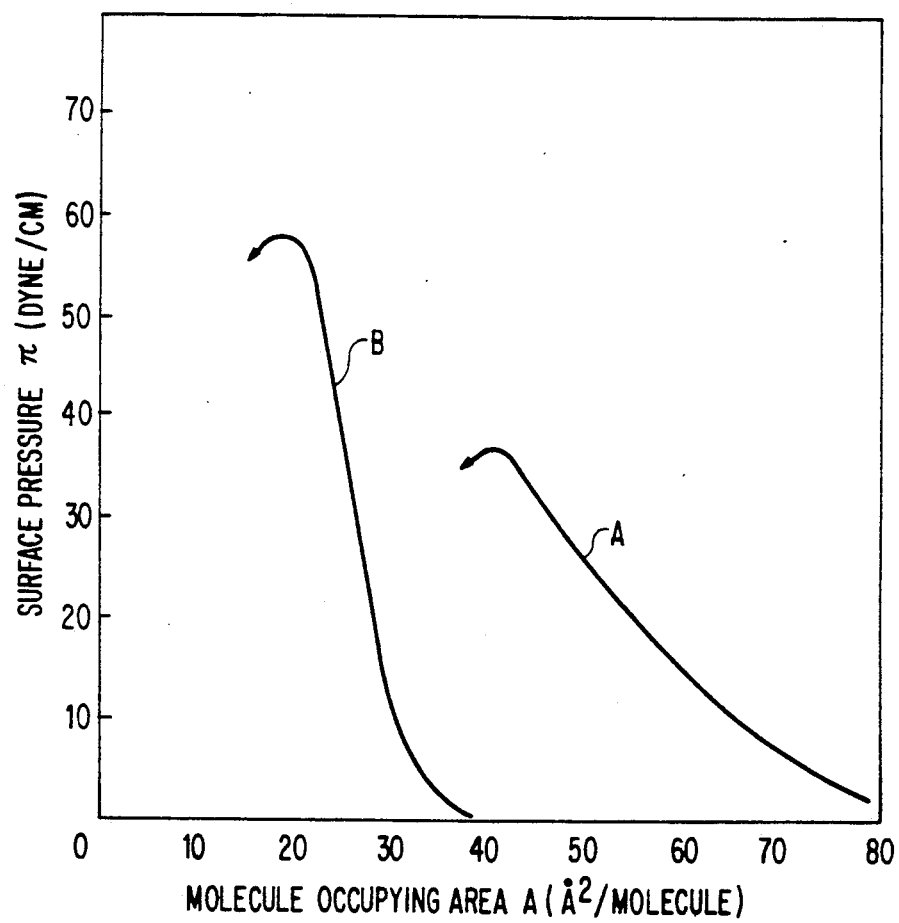
FIG. 1 is a graph illustrating the isothermal characteristics at 20° C. of a surface pressure-molecule occupying area ($\pi$-A), wherein A is a curve for the monomolecular film of the monomer mixture of compounds I-1 and II-1 and B is a curve for the monomolecular film after polymerization at room temperature for 10 hours.

The polymerized monomolecular film or built-up film of the present invention is an ultra-thin film carried on a substrate by various monomolecular film coating methods including the Langmuir Blodgett process, and is characterized by the main chain of the polymer being composed of polypeptides, i.e., chains of amide bonds of amino acids or amino acid derivatives. In the polymerized film of the present invention, amphiphilic amino acid derivatives having a reactive ester group, i.e., electrophilic ester groups, are subjected to condensation polymerization by the following reaction to form the skeleton of the amide bond.

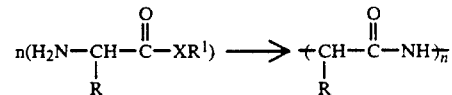

wherein n represents an integer of 2 or greater, and R, R¹ and X are illustrated hereinafter.

When the polymerization of the above-described amino acid derivatives takes place, the rate of polymerization (namely, n being larger or smaller) varies depending on the reaction conditions. The second amphiphilic compounds having a diamino moiety or a diester moiety play a role in forming a much firmer polymerized network to thereby cover the above-described variation in the rate of polymerization. After the chain-lengthening by amide bonds, the remaining ester groups are crosslinked by the second amphiphilic compound having a diamino moiety, or after the chain-lengthening by amide bonds, the remaining amino groups are crosslinked by the second amphiphilic compound having a diester moiety. The second amphiphilic compounds will be illustrated hereinafter.

Now, methods for forming the polymerized thin film of the present invention will be illustrated below.

A method comprising carrying out polymerization at the gas-liquid interface and a method comprising carrying out polymerization on a substrate can be used to form the polymerized thin film.

To carry out polymerization at the gas-liquid interface, a monomolecular film of a monomer mixture of (a) an amphiphilic amino acid ester derivative monomer and (b) an amphiphilic diamino derivative monomer or an amphiphilic diester derivative monomer according to the present invention is prepared by spreading the monomer mixture on a subphase in a trough for the production of a monomolecular film with an appropriate organic solvent. The film is left to stand on the subphase for an appropriate period of time, preferably for 30 minutes to ten-odd hours (for example, about 15 hours). Pure water or a salt solution, such as a buffer solution can be used for the subphase. Preferably, the pH thereof is adjusted to a range of 5 to 9 depending on the equilibrium constant of the ester decomposition of the monomer to be used.

The temperature of the subphase is preferably in the range of from room temperature to 60° C. When the temperature is high, the reaction can be accelerated.

The surface pressure of the monomolecular film during the reaction is kept in the range of preferably 5 to 40 dyne/cm, more preferably 10 to 25 dyne/cm. Generally, the surface pressure is controlled to a given value. If desired, the surface pressure may be increased or reduced as the reaction proceeds. After the completion of the reaction, the polymerized film on the subphase is transferred onto a hydrophilic or hydrophobic substrate by means of the Langmuir-Blodgett process (vertical dipping method) or the horizontal dipping method. When one layer of the film is transferred onto the substrate, a polymerized monomolecular film is formed thereon. When many layers of the film are transferred onto the substrate one by one, a polymerized built-up film is formed thereon.

The second method is a method wherein a monomolecular film of a monomer mixture of (a) an amphiphilic amino acid ester derivative monomer and (b) an amphiphilic diamino derivative monomer or an amphiphilic diester derivative monomer is formed on a subphase and transferred onto a substrate in the manner described above and then the resulting built-up film is left to stand on the substrate to thereby allow polymerization to proceed. When the monomolecular film is to be built up on the substrate in this method prior to the reaction, it is necessary that the subphase is kept under such conditions that the polymerization reaction is inhibited, for example, the subphase is kept at a low pH or under low temperature conditions. The monomers built up on the substrate can be polymerized by treating it under polymerization accelerating conditions, for example, by heating it, treating it with alkaline gas (e.g., $NH_3$) or immersing it in an aqueous alkaline solution.

Of these two polymerization methods, the former gas-liquid interfacial polymerization is preferred from the viewpoint of the permission of reaction. However, the method is not always preferred from the viewpoint of reaction efficiency. They can be properly used depending on the stability of the monomers to be used.

Amphiphilic amino acid ester derivative monomers which are used in the present invention can be represented by the following general formula (I).

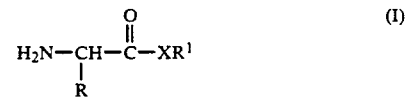

In formula (I), R represents an organic group including a long-chain alkyl group (preferably a straight-chain alkyl group having from 12 to 20 carbon atoms); $XR^1$ is an elimination group whose conjugated acid has a pKa of not higher than 14; X represents —O—, —S—, or —N($R^2$)— (wherein $R^2$ is a hydrogen atom, an alkyl group or an aryl group, and $R^2$ may be combined together with $R^1$ to form a ring which may optionally have a hetero-atom such as nitrogen or an unsaturated bond). Preferably, X is —O—. Examples of $R^1$ include an aryl group (including a substituted aryl group; examples of the aryl group include phenyl and naphthyl; examples of substituent groups include a nitro group and a halogen atom), a haloalkyl group (e.g., monochloromethyl, dichloromethyl, trichloromethyl), an acylamino group (e.g., N-methylacetylamino, N-methylbenzoylamino), —N=$CR^3(R^4)$ (wherein $R^3$ and $R^4$ are each a hydrogen atom, an alkyl group or an aryl group, and the alkyl group and the aryl group may be substituted), an alkenyl group (e.g., —$CH_2$—CH=$CH_2$) and an alkinyl group (e.g., —$CH_2$—C≡CH). Among these groups, the aryl group (including the substituted aryl group) is preferred.

Preferred straight-chain alkyl groups of R are those having from 16 to 20 carbon atoms. When the alkyl group is bonded to the residue of the amino acid through a bonding group, the bonding group is preferably —NHCO—, NHCOO—, NHCONH—, —NHCO—S—, —O—, —S—, —COO—, —$OPO_3^{\ominus}$— or a combination of these groups with the alkyl group.

Preferred examples of the amphiphilic amino acid ester derivative monomers (monomers) represented by formula (I), which can be used in the present invention include, but are not limited to, the following compounds.

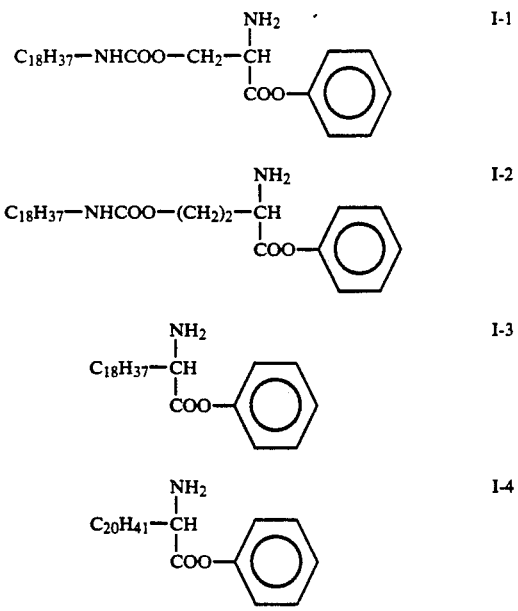

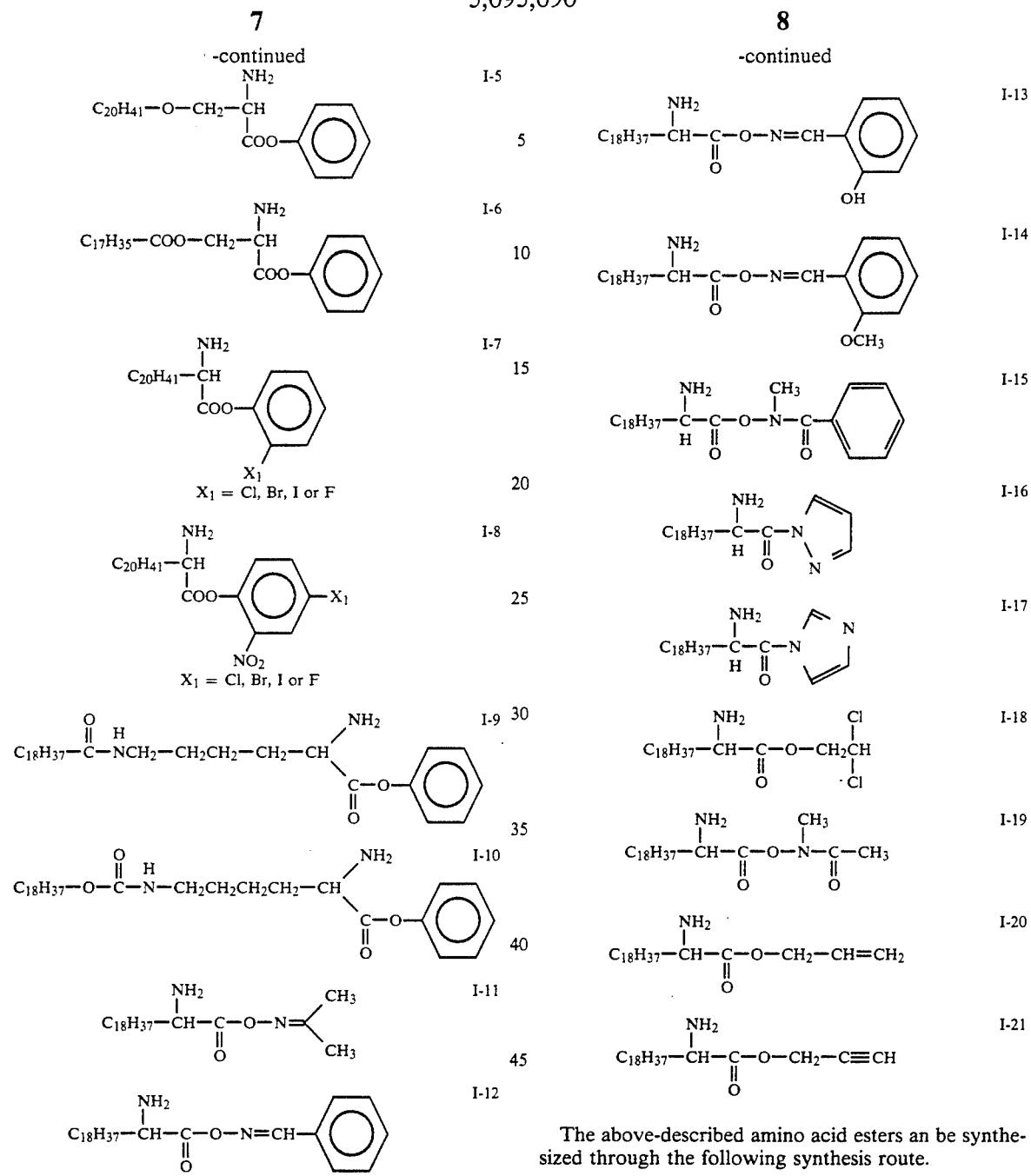
The above-described amino acid esters an be synthesized through the following synthesis route.
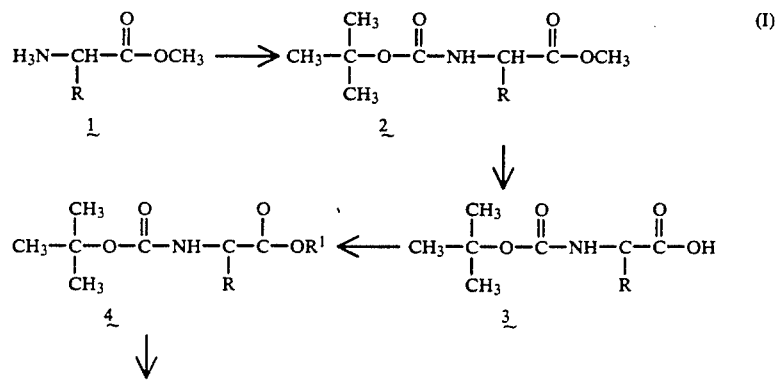

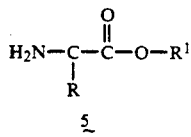

5

The following synthesis example illustrates the synthesis of the compound where $R=C_{18}H_{37}(n)$.

Compound 1' (compound 1 where $R=C_{18}H_{37}(n)$) was synthesized according to the method described in T. Folda, L. Gros, H. Ringodorf, Makromol. Chem. Rapid Commun., Vol. 3, page 167 (1982). M.P. of compound 1'; 94° C. to 98° C. IR spectrum (Nujol): 1760 cm$^{-1}$ (ester carbonyl), 3200 cm$^{-1}$, 1640 cm$^{-1}$, 1550 cm$^{-1}$ (ammonium salt).

35 g (0.093 mol) of compound 1' was dissolved in 200 ml of tetrahydrofuran. 21 g (0.19 mol) of Et$_3$N was added thereto and the mixture was stirred at room temperature for 10 minutes.

243 g (0.14 mol) of di-tert-butyl carbonate (a product of Tokyo Kaseihin) was added thereto and the mixture as such was stirred at room temperature for 10 hours. After completion of the reaction, tetrahydrofuran was distilled off under reduced pressure. Extraction was carried out by adding 200 ml of ethyl acetate and 200 ml of water. This operation was repeated twice. The resulting organic layer was washed with a saturated NaCl solution once and dried over Na$_2$SO$_4$. The organic solvent was distilled off under reduced pressure to give a white crystal. The crystal was recrystallized from ethanol/hexane to obtain 41 g of compound 2' (compound 2 wherein $R=C_{18}H_{37}(n)$).

| | |
|---|---|
| m.p. | 85 to 88° C. |
| IR | 3350 cm$^{-1}$ (NH) |
| (Nujol) | 1760 cm$^{-1}$ (ester) |
| | 1720 cm$^{-1}$ (urethane) |

10 g (0.024 mol) of compound 2' was dissolved in 200 ml of a mixed solution of tetrahydrofuran:CH$_3$OH=2:1. 10.ml of an aqueous solution of 2 g (0.05 mol) of sodium hydroxide was added dropwise thereto. The mixture was stirred at room temperature for 12 hours and acidified to pH=about 4 with dilute hydrochloric acid while cooling it in an ice bath. 200 ml of water was added thereto. Extraction with 100 ml of ethyl acetate was conducted three times. The resulting organic layer was washed with water and dried over Na$_2$SO$_4$. The organic solvents were distilled off under reduced pressure to give a crystal. The crystal was recrystallized from ethyl acetate/hexane to obtain 7.2 g of compound 3' (compound 3 wherein $R=C_{18}H_{37}(n)$).

| | |
|---|---|
| m.p. | 121 to 124° C. |
| IR | 3400 cm$^{-1}$ (NH) |
| (Nujol) | 2800 to 2600 cm$^{-1}$ (OH of carboxylic acid) |
| | 1720 cm$^{-1}$ (carbonyl of carboxylic acid) |
| | 1700 cm$^{-1}$ (urethane) |

Active esters having a long-chain alkyl group described above can be prepared by treating the compound 3 with various alcohols in the presence of dicyclohexylcarbodiimide as a condensing agent.

The following preparation is provided to illustrate the case where phenol is used as a typical example.

1.8 g (0.0042 mol) of compound 3' and 0.4 g (0.0043 mol) of phenol were dissolved in 100 ml of ethyl acetate. 0.95 g (0.0046 mol) of dicyclohexylcarbodiimide (a product of Tokyo Kaseihin) was added thereto. The mixture as such was stirred at room temperature for 12 hours and then cooled with an ice bath. The resulting precipitates were removed by filtration. The mother liquor was concentrated and the residue was purified by means of silica gel column chromatography, eluting with hexane : ethyl acetate=8:1 (by volume) as an eluent to give 1.7 g of compound 4a (compound 4 wherein $R=$

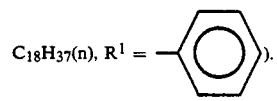

| | |
|---|---|
| m.p. | 125 to 129° C. |
| IR | 3360 cm$^{-1}$ (NH) |
| (Nujol) | 1780 cm$^{-1}$ (ester) |
| | 1695 cm$^{-1}$ (urethane) |
| | 1600 cm$^{-1}$ (substituted benzene) |

1 g of the compound 4a was dissolved in 10 ml of anhydrous chloroform, and the resulting solution was cooled in an ice bath to 0° C. 5 ml of CF$_3$CO$_2$H was added thereto and the mixture was stirred at 0° C. for 30 minutes. The solvent was distilled off under reduced pressure. The resulting white crystal was again dissolved in 20 ml of chloroform, and the chloroform layer was washed with 10 ml of a 5% aqueous solution of NaHCO$_3$ twice. The chloroform layer was then washed with water and dried over Na$_2$SO$_4$. The solvent was distilled off under reduced pressure while using an ice bath to obtain 0.7 g of the desired compound I-3 as a white crystal.

Figure 7:
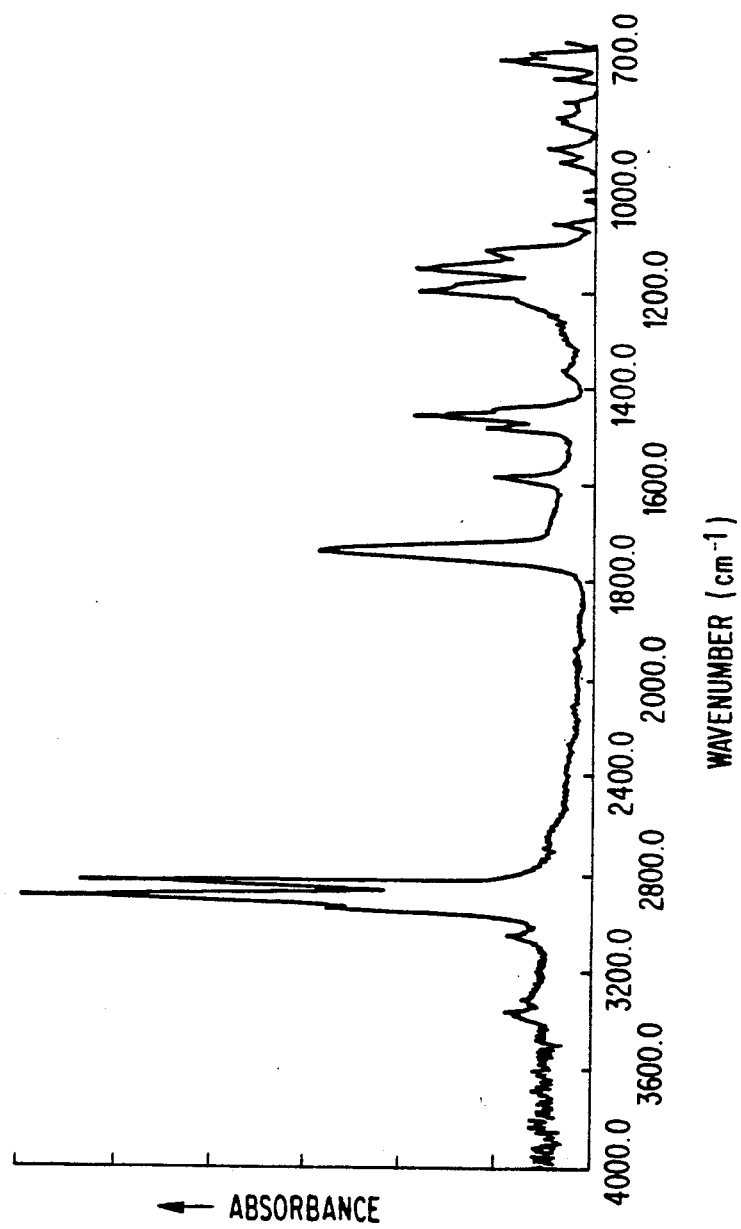
FIG. 7 is a chart showing infrared absorption spectrums of compound I-3.

The compound was decomposed on standing at room temperature. Therefore, the compound was fed to a film preparing stage without purification after the structure was confirmed by IR spectrums (FIG. 7).

In a similar manner to that described above, other compounds were prepared. The compounds were unstable and hence the melting points of their intermediates 4b to 4e were measured.

| Compound | Intermediate | R | R$^1$ | M.P. (°C.) |
|---|---|---|---|---|
| I-18 | 4b | C$_{18}$H$_{37}$(n) | —CH$_2$CH(Cl)Cl | 102 to 103 |
| I-19 | 4c | " | —N(CH$_3$)—C(=O)—CH$_3$ | 99 to 101 |

-continued

| Compound | Intermediate | R | R[1] | M.P. (°C.) |
|---|---|---|---|---|
| I-20 | 4d | " | —CH$_2$—CH=CH$_2$ | 95 to 100 |
| I-21 | 4e | " | —CH$_2$—C≡CH | 85 to 89 |

Amphiphilic diamino compounds which are used in the present invention can be represented by the following general formula (II)

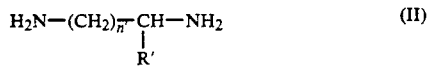

In formula (II), n' represents an integer of from 1 to 8, preferably n' is 4; and R' represents a straight-chain alkyl group having preferably 10 to 20 carbon atoms. When the alkyl group is bonded to the residue of the diamino compound through a bonding group, the bonding group is preferably —NHCO—, —NHCOO—, —NHCONH—, —NHCO—S—, —O—, —S—, —COO—, —OPO$_3^\ominus$— or a combination of these groups with the alkyl group.

Preferred examples of the diamino compounds which can be used in the present invention include, but are not limited to, the following compounds.

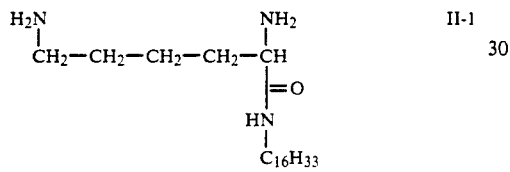

II-1

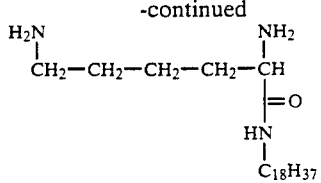

II-2

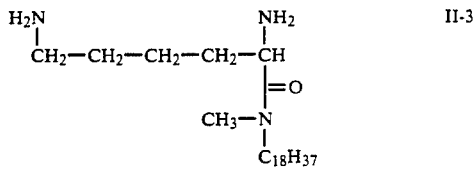

II-3

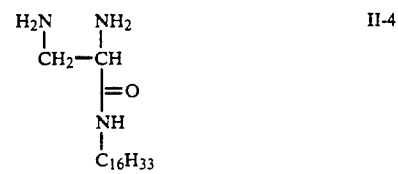

II-4

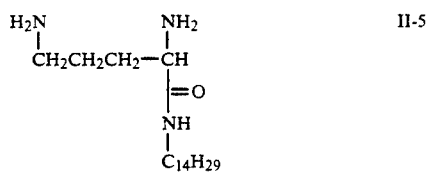

II-5

The mixing ratio by mole of the amphiphilic amino acid ester of formula (I) and the amphiphilic diamino compound of formula (II) is in the range of (I) : (II) = 1:1 to 20:1, particularly preferably 3:1 to 15:1.

The following synthesis examples illustrate the synthesis of the amphiphilic diamino derivatives of formula (II).

Synthesis of compound II-1

Synthesis route

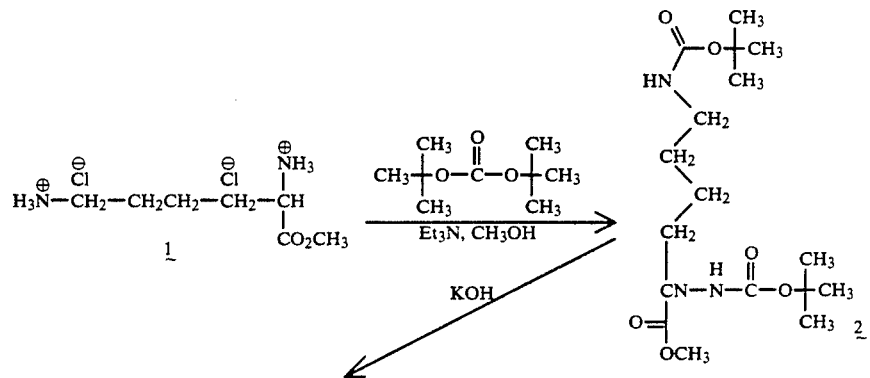

Synthesis of compound II-1

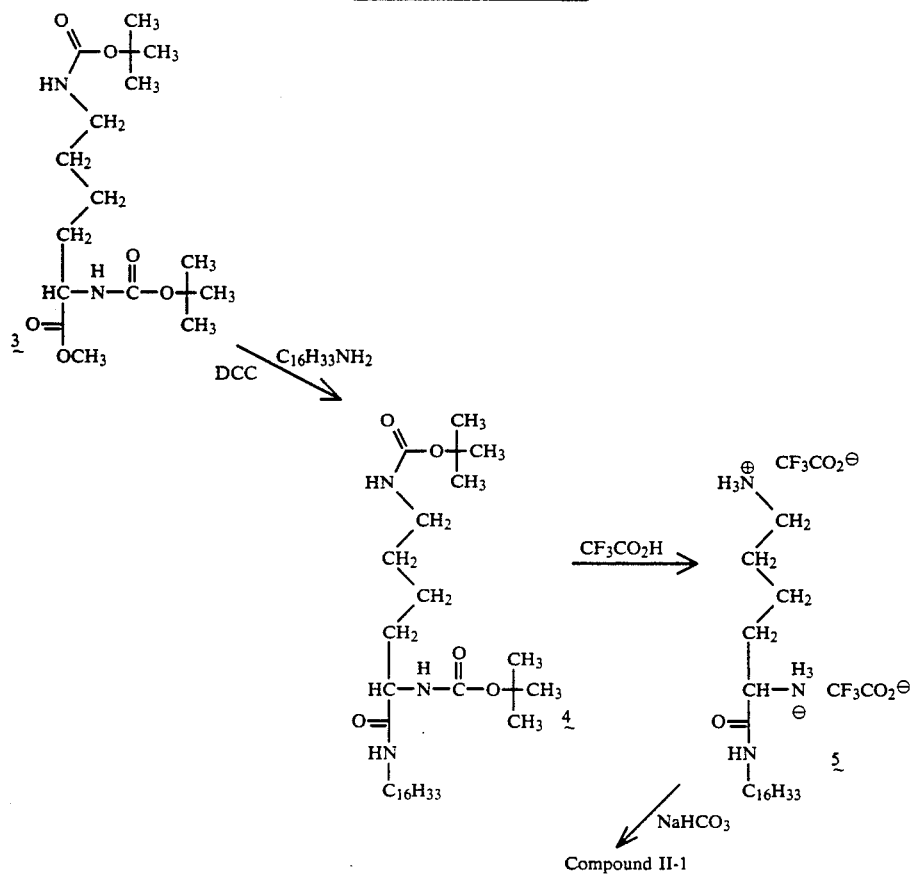

Compound II-1

23.2 g (0.1 mol) of compound 1 (commercially available) was dissolved in 200 ml of methanol. 20.2 g (0.2 mol) of triethylamine was added thereto. 30.4 g (0.2 mol) of di-tert-butyl carbonate was added thereto and the mixture was stirred for 12 hours. The solvent was distilled off under reduced pressure. 300 ml of water was added to the residue. Extraction was repeatedly carried out with ethyl acetate.

The ethyl acetate layer was washed with water and dried over $Na_2SO_4$. The solvent was distilled off under reduced pressure. The resulting colorless oil was purified by means of silica gel column chromatography, eluting with hexane : ethyl acetate =5:1 (by volume) as an eluent to give 28 g of compound 2 as colorless oil.

IR (Neat): 3300 cm$^{-1}$, 1735 cm$^{-1}$, 1700 cm$^{-1}$.

18 g (0.05 mol) of compound 2 was dissolved in 300 ml of EtOH. An aqueous solution of 9.85 g (0.15 mol) of KOH (85% content) in 20 ml of water was added thereto and the mixture was stirred at room temperature for 3 hours. 300 ml of water was added thereto and EtOH was distilled off under reduced pressure. The pH of the residue was adjusted to 3 to 4 by adding dilute hydrochloric acid. Extraction was repeatedly carried out with ethyl acetate. The extract was dried over $Na_2SO_4$. The solvent was distilled off under reduced pressure to give 15 g the desired compound 3 as a viscous oil.

IR (Neat): 3100 cm$^{-1}$, 1710 cm$^{-1}$, 1695 cm$^{-1}$.

10.4 g (0.03 mol) of compound 3 was dissolved in anhydrous tetrahydrofuran. The solution was cooled in an ice bath to 0° C., 6.2 g (0.03 mol) of dicyclohexacarbodiimide (DCC) was added thereto and the mixture was stirred at 0° C. for 30 minutes.

The ice bath was then removed, 7.2 g (0.03 mol) of $C_{16}H_{33}NH_2$ was added thereto and the mixture was stirred at room temperature for 12 hours. Tetrahydrofuran was distilled off under reduced pressure. The residue was dissolved in chloroform and any insoluble matter was removed by filtration. The residue was purified by means of silica gel column chromatography (eluting with hexane : ethyl acetate =2:1 (by volume) as an eluent) to give 15 g of the desired compound 4 as a colorless oil.

IR (Neat): 3520 cm$^{-1}$, 1700 cm$^{-1}$, 1640 cm$^{-1}$, 1570 cm$^{-1}$.

5.8 g (0.01 mol) of compound 4 was dissolved in 100 ml of $CH_2Cl_2$, The solution was cooled to 0° C. and stirred. 20 ml of $CF_3CO_2H$ was added thereto and the mixture was stirred at 0° C. for 30 minutes. Volatile matter was distilled off under reduced pressure to give 5.6 g of the desired compound 5 as a colorless crystal. M.P. 145° C.

IR (KBr): 3320 cm$^{-1}$, 1670 cm$^{-1}$, 1640 cm$^{-1}$, 1570 cm$^{-1}$.

3 g of compound 5 was dissolved in $CH_2Cl_2$. The solution was treated with a 5% aqueous solution of $NaHCO_3$ twice. The separated fraction was washed with saturated saline solution and dried over $Na_2CO_3$. The solvent was distilled off under reduced pressure to give 2.1 g of compound II-1 as an oil. The compound was unstable. Hence, the compound was fed to a subsequent stage without purification.

IR (Neat): 3320 cm$^{-1}$, 1640 cm$^{-1}$, 1570 cm$^{-1}$.

In a similar manner to that described above, compounds II-2, II-3 and II-5 were prepared. These three compounds were a colorless oil.

Amphiphilic diester compounds which are used in the present invention can be represented by the following general formula (III).

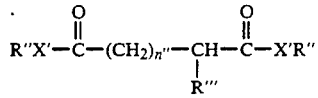
(III)

In formula (III), X'R" represents an elimination group whose conjugated acid has a pKa of not higher than 16; X' represents —O—, —S— or —N(R$^5$)— (wherein R$^5$ is a hydrogen atom, an alkyl group or an aryl group and R$^5$ may be combined together with R" to form a ring which may optionally have a hetero-atom such as nitrogen or an unsaturated bond). Preferably, X' is —O—. Examples of R" include an alkyl group (e.g., methyl, ethyl), an aryl group (including a substituted aryl group, e.g., phenyl, naphthyl and examples of substituent groups including a nitro group and a halogen atom), a haloalkyl group (e.g., monochloromethyl, dichloromethyl, trichloromethyl), an acylamino group (e.g., N-methylacetylamino, N-methylbenzoylamino), —N=CR$^6$(R$^7$) (wherein R$^6$ and R$^7$ are each a hydrogen atom, an alkyl group or an aryl group and the alkyl group and the aryl group may be substituted), an alkenyl group (e.g., —CH$_2$—CH=CH$_2$) and an alkinyl group (e.g., —CH$_2$—C≡CH). Among these groups, the aryl group including the substituted aryl group is preferred.

In formula (III), n" represents 0 or an integer of 1 to 3.

Preferred straight-chain alkyl groups represented by R''' are those having from 10 to 20 carbon atoms. When the alkyl group is bonded to the residue of the diester compound through a bonding group the bonding group is preferably —NHCO—, —NHCOO—, —NHCONH—, —NHCO—S—, —O—, —S—, —COO—, —OPO$_3$$^\ominus$— or a combination of these groups with the alkyl group.

Preferred examples of the diester compounds (monomers) which can be used in the present invention include, but are not limited to, the following compounds.

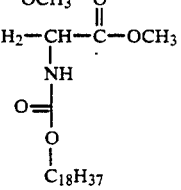
III-1

-continued

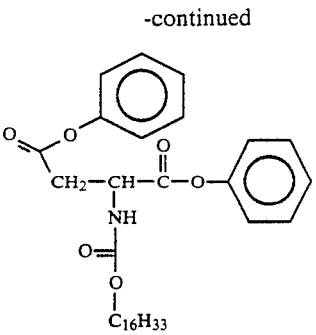
III-2

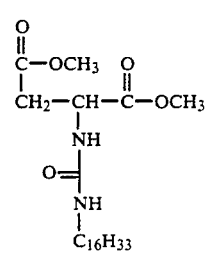
III-3

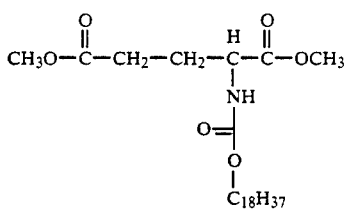
III-4

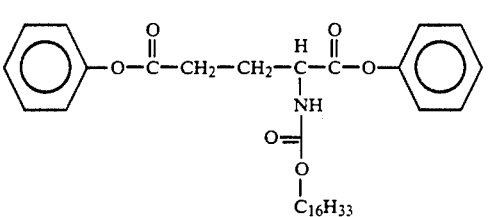
III-5

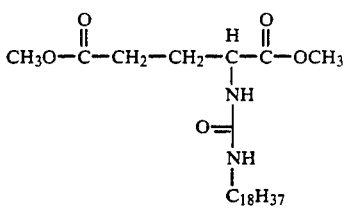
III-6

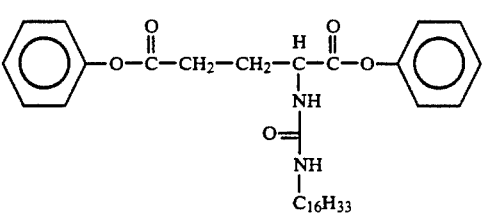
III-7

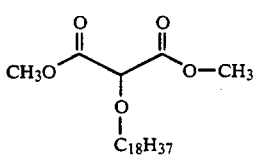
III-8

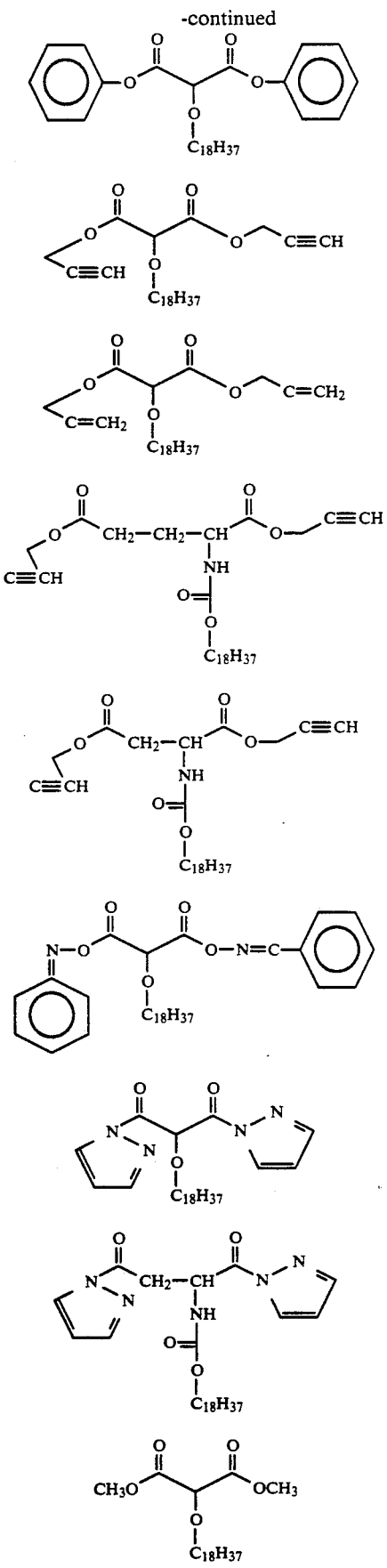

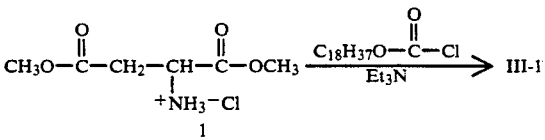

The mixing ratio by mole of the amphiphilic amino acid ester of formula (I) and the amphiphilic diester derivative of formula (III) is in the range of (I) : (III) = 1:1 to 20:1, particularly preferably 3:1 to 15:1.

The following synthesis Example illustrates the synthesis of the amphiphilic diester derivative.

Synthesis of compound III-1

Synthesis route $$CH_3O-\overset{O}{\overset{\|}{C}}-CH_2-\underset{\underset{^+NH_3^-Cl}{|}}{CH}-\overset{O}{\overset{\|}{C}}-OCH_3 \xrightarrow[Et_3N]{C_{18}H_{37}O-\overset{O}{\overset{\|}{C}}-Cl} III-1$$

$\underline{1}$ 5.0 g (0.025 mol) of trichloromethyl chloroformate was dissolved in 200 ml of tetrahydrofuran (THF). The solution was cooled to $-5°$ C. 13.5 g (0.05 mol) of stearyl alcohol and 5 g (0.05 mol) of triethylamine were added dropwise thereto with stirring. After 30 minutes, an ice bath was removed and the mixture was stirred at room temperature for one hour. Volatile matter was distilled off under reduced pressure by using an aspirator, 50 ml of THF was added to the oily residue. The resulting solution was gradually added to 100 ml of a THF solution containing 9 g (0.05 mol) of compound 1 and 12 g (0.12 mol) of triethylamine. The mixture was stirred at room temperature for one hour. THF was then distilled off under reduced pressure. Water was added to the residue. Extraction was repeatedly carried out with ethyl acetate. The ethyl acetate layer was washed with a saline solution and dried over $Na_2SO_4$. The solvent was distilled off under reduced pressure. The residue was purified by means of silica gel column chromatography, eluting with hexane : ethyl acetate = 2:1 (by volume) to give 7.5 g of the desired compound III-1 as a colorless oil.

IR (Neat) spectrum: 1735 $cm^{-1}$ (carbonyl of ester), 1700 $cm^{-1}$ (carbonyl of urethane).

In a similar manner to that described above, compounds III-3, III-4 and III-6 were prepared. These three compounds were a colorless oil.

Various organic resin materials or inorganic materials having a hydrophilic or hydrophobic surface can be used as substrates (supports) to be coated with the polymerized or unpolymerized monomolecular film or built-up film in the present invention. These materials may be flat, or may have porous or fibrous three-dimensional network structure.

Examples of the flat materials include electrically conductive materials such as metals, vitreous inorganic materials (e.g., glass quarts), other inorganic insulating materials, various inorganic and organic crystals, inorganic semiconductors ($SnO_2$, $In_2O_3$, ZnO, $TiO_2$, $WO_3$, GaAs, Si), organic semiconductors, organic electrical conductors, organic polymers and composite materials thereof. The materials may be electrodes connected with external electric circuits or other components such as sensors (e.g., field effect transistor).

Porous materials are useful as substrates when mainly used as permeable films or filters. Examples of the porous materials include organic and inorganic microporous filters, cellulose resin films and various porous polymer films.

Examples of solvents for spreading the monomolecular film, which are used in the present invention include conventional volatile nonpolar organic solvents, such as chloroform, dichloromethane, benzene, toluene and ether and mixture thereof with hydrophilic polar solvents, such as alcohols and water.

Various building-up methods including the LB process can be used for coating the surface of the substrate or the support with the monomolecular film on a subphase. The LB process which is a vertical dipping method is described in *J. Am. Chem. Soc.*, Vol. 57, page 1007 (1935); G. L. Gains, Jr., *Insoluble Monolayers at Liquid-Gas Interfaces*, (Interscience), New York (1966); and *Material Technique*, Vol. 4, page 261 written by Kiyonari Fukuda (1986).

In addition thereto, other methods such as a horizontal dipping method and a rotating dipping method (e.g., described in JP-A-60-189929, JP-A-61-42394) can be used as coating methods. The built-up film can be obtained by carrying out repeatedly an operation of coating the substrate with the monomolecular film.

An improved horizontal dipping method described in Japanese Patent Application No. 63-54680 (corresponding to JP-A-1-228539) or continuous building-up method described in JP-A-60-209245 may be used for effectively carrying out building-up.

The present invention is now illustrated in greater detail by reference to the following examples which, however, are not to be construed as limiting the invention in any way.

Unless otherwise indicated, all percents, ratios, parts, etc., are by weight.

EXAMPLE 1

Figure 2:
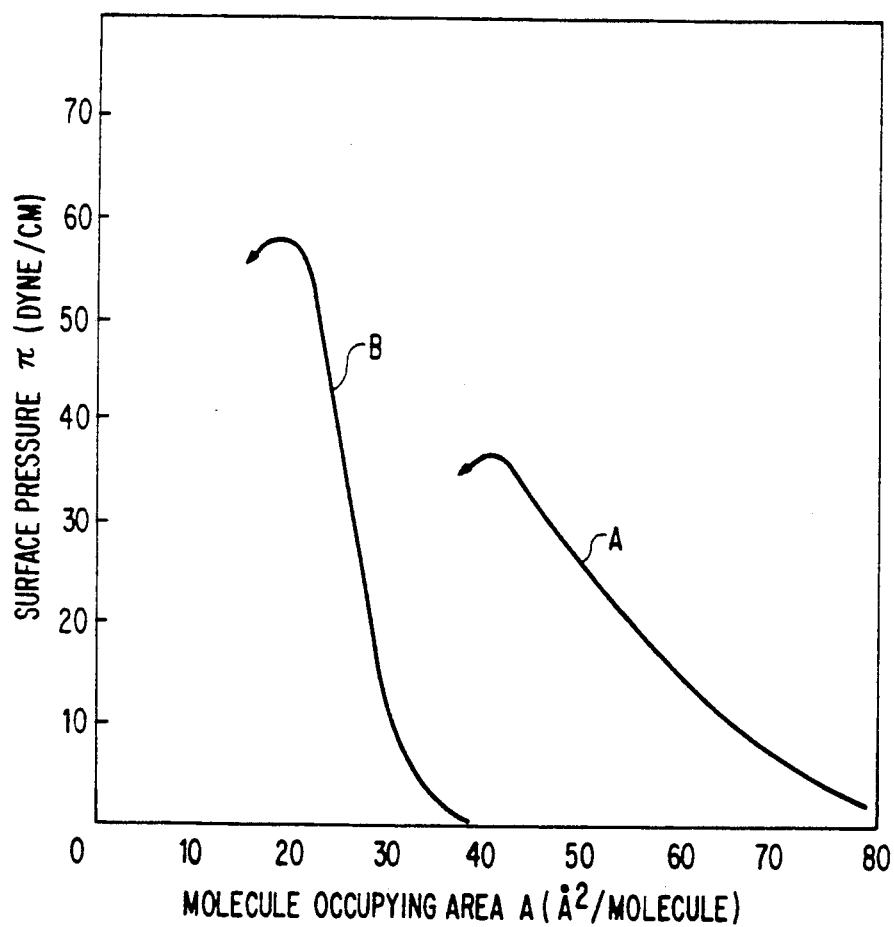
FIG. 2 is a graph illustrating the isothermal characteristics at 20° C. of a surface pressure-molecule occupying area ($\pi$-A), wherein A is a curve for the monomolecular film of the monomer mixture of compounds I-1 and III-1 and B is a curve for the monomolecular film after polymerization at room temperature for 10 hours.

Compound I-1 as the amphiphilic amino acid phenyl ester and compound II-1 as the amphiphilic diamino compound or compound III-1 as the amphiphilic diester compound were mixed in a ratio of 20:1. Each of the mixture consisting of compounds I 1 and II-1 and the mixture consisting of compounds I-1 and III-1 was dissolved in dichloromethane to a concentration of 1 mM, thus preparing each of the spreading solutions. Each solution was spread on the subphase of a $10^{-3}$ M phosphate buffer solution (pH 7.4) by using Langmuir's film balance to prepare a monomolecular film. Immediately after the preparation, the monomolecular film was compressed at a rate of 10 cm$^2$/min by means of belt drive barrier. The surface pressure-molecule occupying area ($\pi$-A) characteristics at 20° C. of each of the monomolecular film comprising the monomer mixture of compounds I-1 and II-1 and the monomolecular film comprising the monomer mixture of compounds I-1 and III-1 were measured. The results obtained are set forth in curve A of FIG. 1 and in curve A of FIG. 2. It was seen from the $\pi$-A characteristics that good monomolecular films were formed. Each monomolecular film was left to stand on the subphase of the buffer solution under a given surface pressure of 15 dyne/cm at room temperature for about 10 hours to thereby allow polymerization and crosslinking to proceed. After standing, the $\pi$-A characteristics were again measured. The results obtained are set forth in curve B of FIG. 1 with respect to the polymerized film of the monomolecular film comprising the monomer mixture of compounds I-1 and II-1 and in curve B of FIG. 2 with respect to the polymerized film of the monomolecular film comprising the monomer mixture of compounds I-1 and III-1. It is clear from the curves A and B that the molecule was densified by polymerization, the film shrunk, the breaking strength was improved and hence the film was strengthened.

Each of the polymerized films was compressed to 30 dyne/cm, and 40 layers thereof were built up on a gold-deposited glass substrate by means of a horizontal dipping method. Fourier transfuction infrared absorption spectrums of each built-up film were measured on the gold surface by a reflection absorption method. It was found that absorption bands specific to the phenyl ester disappeared, absorption bands showing the formation of amide bonds appeared at 1650 to 1700 cm$^{-1}$ and hence a polypeptide was formed by polymerization. Further, the spectrums of samples built up on a silicon substrate were measured by the permeation method and compared with the above spectrums. It was found in both films that in the reflection method, absorption in C—H expansion of the long-chain alkyl group was remarkably lowered in comparison with absorption in C=O expansion of the amide. Hence, the axis of the long-chain alkyl group was orientated in the direction perpendicular to the plane of the substrate. Accordingly, it could be confirmed that molecular arrangement was maintained.

EXAMPLE 2

Figure 3:
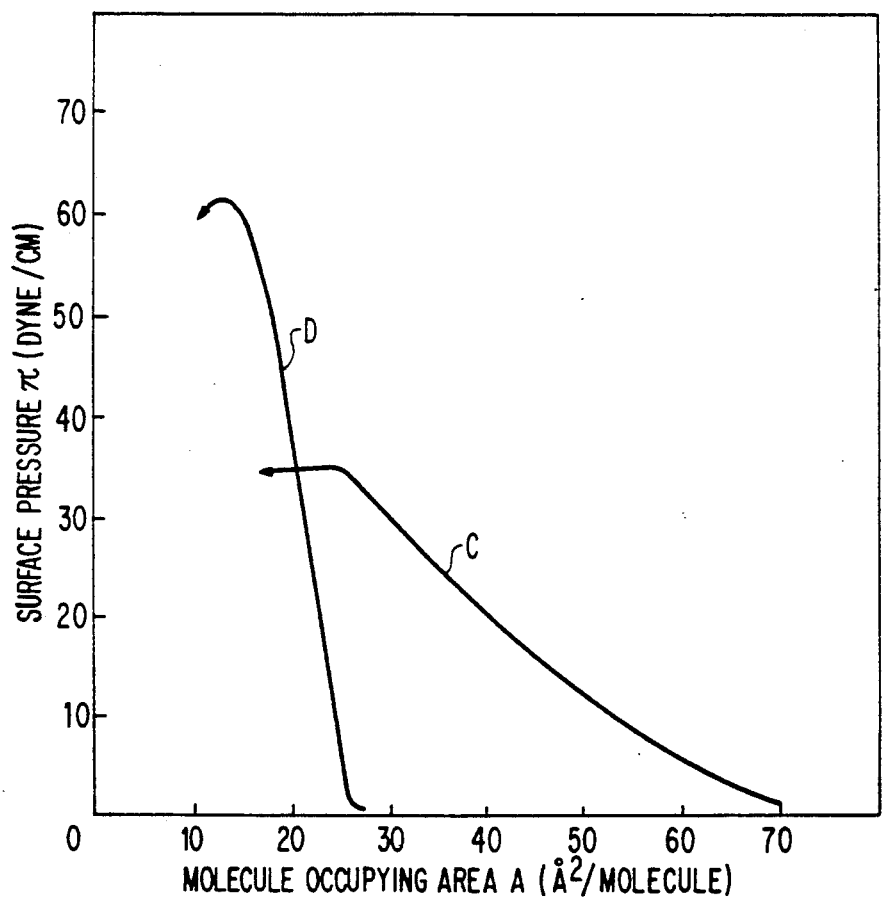
FIG. 3 is a graph illustrating the $\pi$-A isothermal characteristics at 20° C., wherein C is a curve for the monomolecular film of the monomer mixture of compounds I-3 and II-5 and D is a curve for the monomolecular film after polymerization at room temperature for 8 hours.
Figure 4:
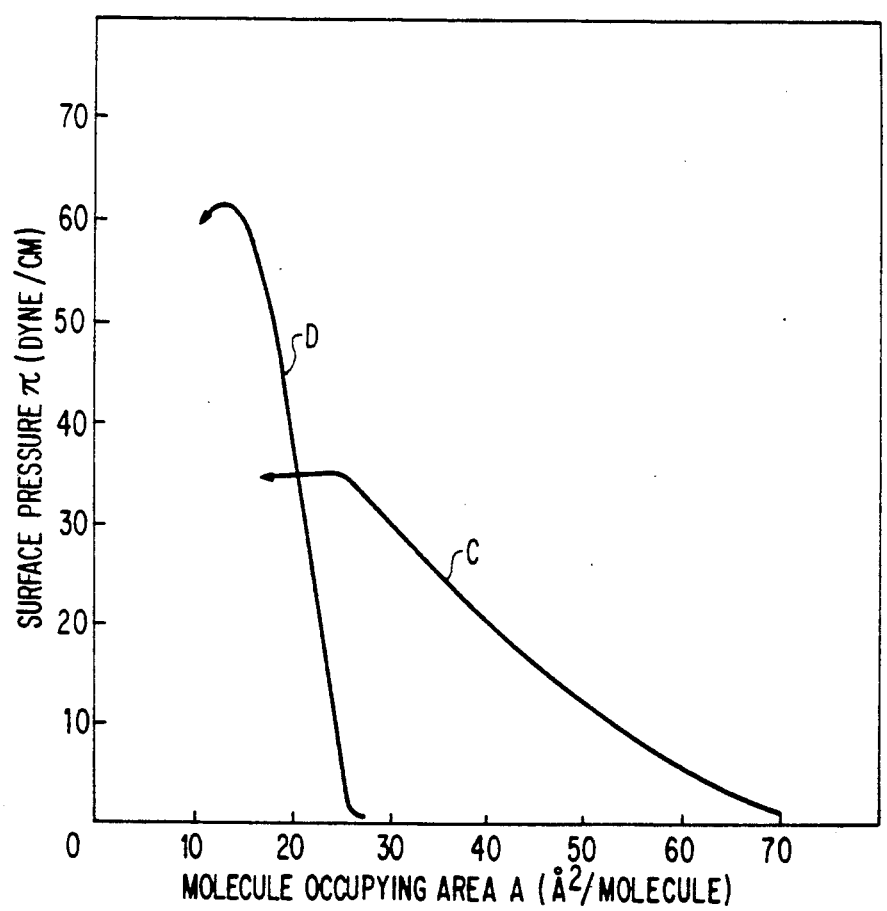
FIG. 4 is a graph illustrating the $\pi$-A isothermal characteristics at 20° C., wherein C is a curve for the monomolecular film of the monomer mixture of compounds I-3 and III-18 and D is a curve for the monomolecular film after polymerization at room temperature for 8 hours.

Compound I-3 as the amino acid phenyl ester and compound II-5 as the amphiphilic diamino compound or compound III-18 as the amphiphilic diester compound were used and each of the spreading solutions was prepared in the same way as in Example 1. The $\pi$-A characteristics at 20° C. of each of the monomolecular film comprising the monomer mixture of compounds I-3 and II-5 and the monomolecular film comprising the monomer mixture of compounds I-3 and III-18 were measured. The results obtained are set forth in curve C of FIG. 3 and in curve C of FIG. 4. .Each monomolecular film was left to stand on the subphase having a pH of 7.4 at 35° C. under a constant surface pressure of 25 dyne/cm for about 8 hours to thereby allow polymerization to proceed. After the polymerization, the $\pi$-A characteristics were again measured. The results obtained are set forth in curve D of FIG. 3 with respect to the polymerized film of the monomolecular film comprising the monomer mixture of compounds I-3 and II-5 and in curve D of FIG. 4 with respect to the polymerized film of the monomolecular film comprising the monomer mixture of compounds I-3 and III-18. It is clear from curves C and D that the film shrunk and was strengthened.

After a lapse of given times, about 40 layers of each monomolecular film were built up on a Si wafer substrate by the horizontal dipping method to measure polymerization rate. The infrared absorption spectrums of the built-up film were measured by the permeation method, and the rate of decrease in the characteristic absorption ($\sim$1750 cm$^{-1}$) of the phenyl ester was examined. It was found in both films that about 50% of the ester disappeared after reaction for 10 minutes, about 90% of the ester disappeared after reaction for 60 minutes, at most 100% of the ester disappeared after reaction for 8 hours and amide bonds were formed.

COMPARATIVE EXAMPLE

For the purpose of comparison, the following amphiphilic amino acid methyl ester monomer was used. In the same way as in Example 1, a monomolecular film was formed on the subphase and polymerized.

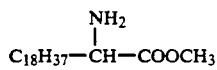

An aqueous buffer solution having a pH of 7.4 was used as a subphase, and measurements were made at the two points of 20° C. and 35° C. The π-A characteristics at 20° C. of the above monomer were similar to those of compound I-3, and the breaking pressure was about 35 dyne/cm. The monomolecular film was left to stand on the subphase at 20° C. and 35° C. under constant surface pressure of 15 dyne/cm for about 2 hours. However, change in the area of the film was scarcely used.

In the same way as in Example 2, 40 layers of the film were built up on the Si wafer substrate. FT-IR spectrums were measured. In both cases of temperatures, the built-up film exhibited IR spectrums wherein the strong absorption ($\sim 1730$ cm$^{-1}$) of the ester remained, and amide bonds were scarcely formed. Further, the monomolecular film was left to stand on a subphase having a pH of 9 under a surface pressure of 15 dyne/cm for about 20 hours, the pH value elevating the activity of the ester. Thereafter, the monomolecular film was built up in the same way as in the above-described operation. Absorption spectrums were measured. Weak broad absorption at 1600 to 1700 cm$^{-1}$ due to apparently the formation of amide bonds were observed. However, the sharp absorption of the ester group was still left and the reaction was not completed. It was considered that the polymerization rate of the alkyl ester derivative was lowered by a number of at least two figures than that of the aryl ester derivative of the presenting invention.

EXAMPLE 3

In the same way as in Example 1, 4 to 16 layers of each of the polymerized films of the compounds used in Example 1 were built up on the surface of a glassy carbon electrode under 30 dyne/cm. The permeability was evaluated on the basis of an electrochemical measurement.

A metal ion as an object to be permeated was chosen as the substrate. The polymerized film-coated glassy carbon electrode was immersed in a neutral electrolytic solution consisting of 1 mM K$_3$Fe(CN)$_6$ and 10 mM KNO$_3$. The rate of FE$^{3+}$ ion to be passed through the polymerized film was measured by means of cyclic voltammetry of oxidation-reduction current of Fe$^{3+}$/Fe$^{2+}$. The electrode potential was controlled against a saturated calomel electrode. Electrolysis was carried out under an N$_2$ gas purge. The voltammogram was measured after the potential was repeatedly scanned about 30 times. Voltammetry was carried out for the polymerized film of the present invention as well as the film built up on the electrode immediately after spreading the monomolecular film of the monomer before polymerization. Both were compared with each other.

Figure 5A:
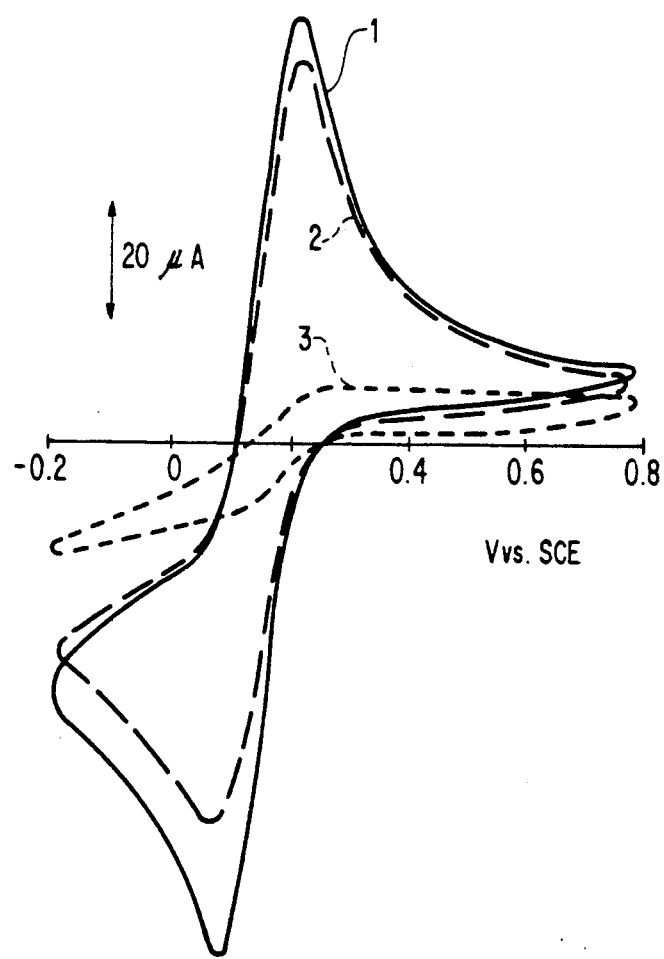
FIG. 5A is a Voltammograph of the built-up film of the monomer mixture of compounds I-1 and II-1, wherein curve 1 is for the case where there is no film, curve 2 is for a film composed of 9 layers, and curve 3 is for a film composed of 14 layers.
Figure 5B:
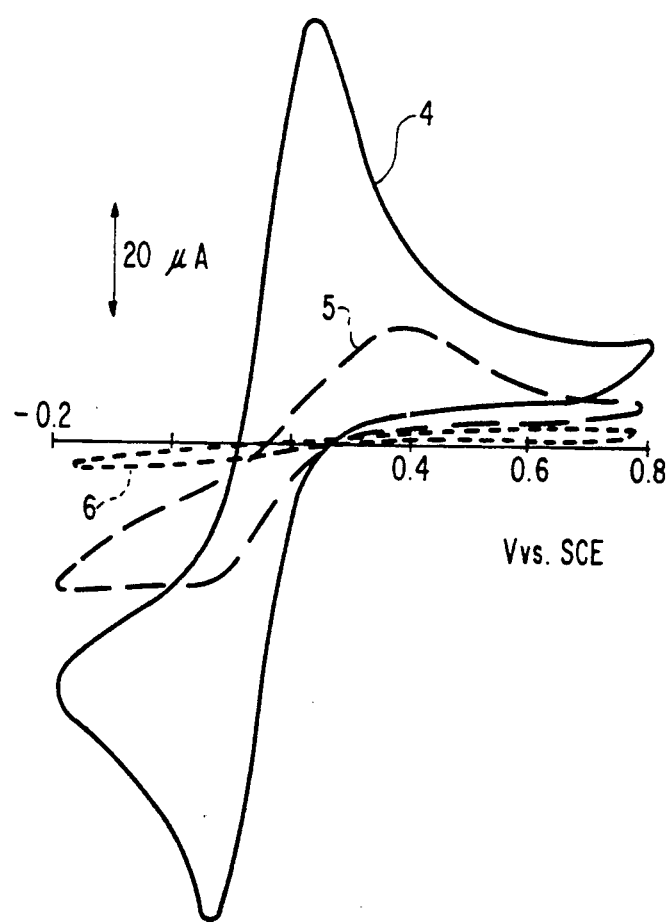
FIG. 5B is a Voltammograph of the polymerized built-up film of the monomer mixture of compounds I-1 and II-1, wherein curve 4 is for the case where there is no film (the same as 1), curve 5 is for a film composed of 3 layers, and curve 6 is for a film composed of 7 layers.

FIG. 5A and FIG. 5B show the results on the built-up film of the monomolecular film comprising the monomer mixture of compounds I-1 and II-1 and the polymerized built-up film thereof, respectively.

Figure 6A:
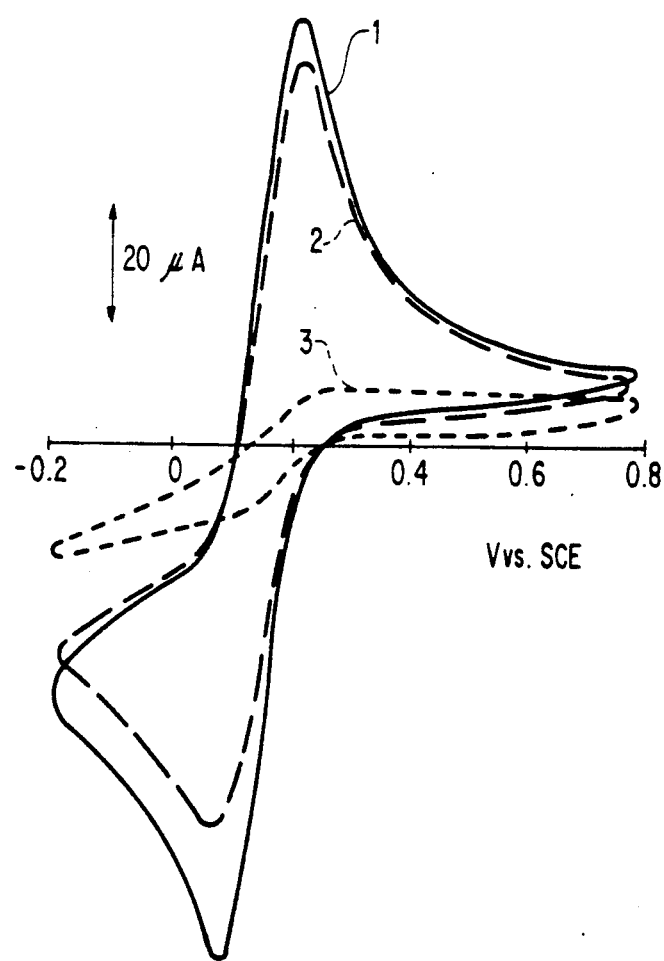
FIG. 6A is a Voltammograph of the built-up film of the monomer mixture of compounds I-1 and III-1, wherein curve 1 is for the case where there is no film, curve 2 is for a film composed of 8 layers, and curve 3 is for a film composed of 16 layers.
Figure 6B:
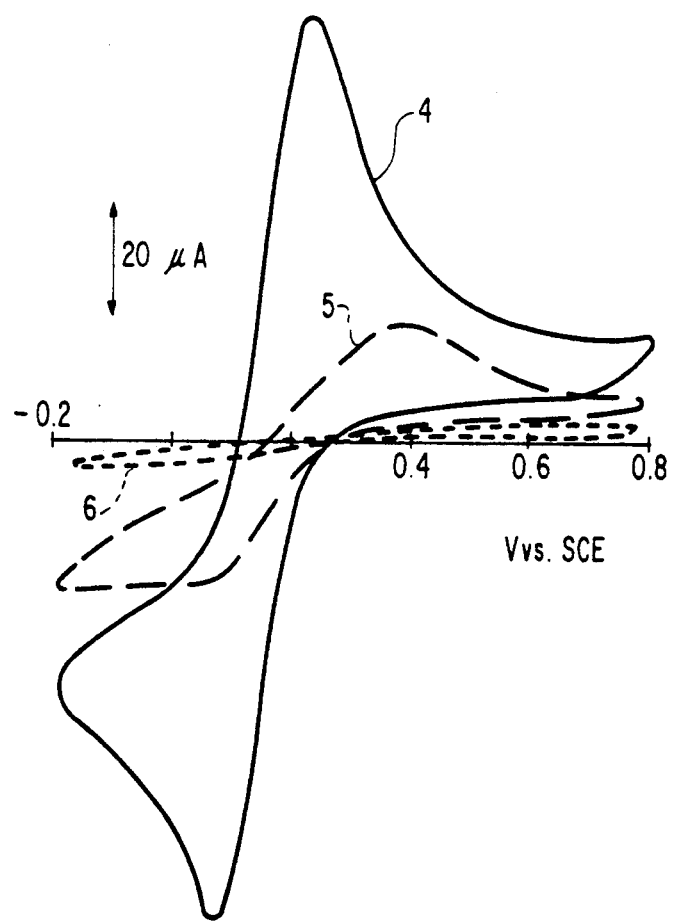
FIG. 6B is a Voltammograph of the polymerized built-up film of the monomer mixture of compounds I-1 and III-1, wherein curve 4 is for the case where there is no film (the same as 1), curve 5 is for a film composed of 4 layers, and curve 6 is for a film composed of 8 layers.

FIG. 6A and FIG. 6B show, the results on the built-up film of the monomolecular film comprising the monomer mixture of compounds I-1 and III-1 and the polymerized built-up film thereof, respectively.

In the built-up film of the monomer (FIG. 5A and FIG. 6A), the peak of current value (corresponding to the amount of Fe$^{3+}$ passed through the film), shown by the cyclic voltammogram, was beginning to cause a marked lowering in the peak value when the number of layers was about 8 (curve 2). When 16 layers were built up (curve 3), the value was lowered to about 1/7 of the peak. In the polymerized film, i.e., polypeptide film (FIG. 5B and FIG. 6B), the current value was lowered to about 1/5 by the building-up of 4 layers (curve 5) and reduced by about two orders by 8 layers (curve 6).

Thus, it is clear in both cases that a remarkable permeation-inhibiting effect can be obtained by polymerization. The voltammogram of the methyl ester of the Comparative Example was measured. The current value was lowered to only ½ to ⅓ by the building up of 8 layers. Therefore, the current-inhibiting effect was low.

While the present invention has been described in detail and with reference to specific embodiments thereof, it is apparent to one skilled in the art that various changes and modifications can be made therein without departing from the spirit and scope of the present invention.

What is claimed is:

1. A polypeptide thin film obtained by polymerizing a monomolecular film comprising a monomer mixture of
   (a) an amphiphilic compound having a hydrophobic moiety and a hydrophilic moiety having an amino acid ester derivative structure per molecule represented by formula (I), wherein a corresponding conjugated acid of an elimination group of said amino acid ester derivative structure has a pKa of not higher than 14:

wherein R represents an organic group including a long-chain alkyl group, XR$^1$ is an elimination group having a conjugated acid that has a pKa of not hither than 14, X represents —O—, —S—, or —N(R$^2$)—, wherein or R$^2$ is a hydrogen atom, an alkyl group or an aryl group, R$^2$ is combined with R$^1$ to form a ring, and R$^1$ represents an aryl group, a haloalkyl group, an acylamino group, —N=CR$^3$(R$^4$), wherein R$^3$ and R$^4$ are each a hydrogen atom, an alkyl group or an aryl group, an alkenyl group or an alkinyl group, and
   (b) an amphiphilic compound having two amino groups per molecule represented by formula (II):

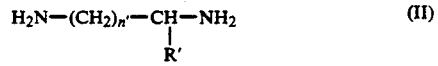

wherein n' represents an integer of from 1 to 8 and R' represents a straight-chain alkyl group, or a built-up film of said monomolecular film.

2. A polypeptide thin film as claimed in claim 1, wherein said amphiphilic compound having a hydrophobic moiety and a hydrophilic moiety having an amino acid ester derivative structure per molecule of formula (I) and said amphiphilic compound having two amino groups per molecule of formula (II) have a mixing ratio by mole in the range of (I):(II)=1:1 to 20:1.

3. A polypeptide thin film as claimed in claim 2, wherein the mixing ratio is in the range of (I):(II)=3:1 to 15:1.

* * * * *